US012614716B2

(12) United States Patent
Adams et al.

(10) Patent No.: US 12,614,716 B2
(45) Date of Patent: Apr. 28, 2026

(54) 2,5-DIMERCAPTO-1,3,4-THIADIAZOLE (DMTD) ZINC SALT DERIVATIVES

(71) Applicants: The Lubrizol Corporation, Wickliffe, OH (US); Ohio State Innovation Foundation, Columbus, OH (US)

(72) Inventors: Paul E. Adams, Willoughby, OH (US); Shiyu Zhang, Columbus, OH (US); Christopher M. Rasik, Cleveland, OH (US); Madison Tuttle, Columbus, OH (US)

(73) Assignees: The Lubrizol Corporation, Wickliffe, OH (US); Ohio State Innovation Foundation, Columbus, OH (US)

( * ) Notice: Subject to any disclaimer, the term of this patent is extended or adjusted under 35 U.S.C. 154(b) by 696 days.

(21) Appl. No.: 18/022,629

(22) PCT Filed: Aug. 24, 2021

(86) PCT No.: PCT/US2021/047272
§ 371 (c)(1),
(2) Date: Feb. 22, 2023

(87) PCT Pub. No.: WO2022/046718
PCT Pub. Date: Mar. 3, 2022

(65) Prior Publication Data

US 2023/0312497 A1 Oct. 5, 2023

Related U.S. Application Data

(60) Provisional application No. 63/070,598, filed on Aug. 26, 2020.

(51) Int. Cl.
*H01M 4/24* (2006.01)
*C07D 285/125* (2006.01)
*H01M 4/60* (2006.01)
*H01M 10/36* (2010.01)

(52) U.S. Cl.
CPC ........ *H01M 4/244* (2013.01); *C07D 285/125* (2013.01); *H01M 4/60* (2013.01); *H01M 10/36* (2013.01)

(58) Field of Classification Search
CPC ...... H01M 10/36; H01M 4/60; C07D 285/125
See application file for complete search history.

(56) References Cited

U.S. PATENT DOCUMENTS 4,992,456 A * 2/1991 Diehr .................... A01N 43/82 514/342
5,298,177 A * 3/1994 Stoffa ................ C10M 169/048 508/400
6,187,475 B1 * 2/2001 Oh .......................... H01M 6/04 429/232
6,340,539 B1 * 1/2002 Yamaguchi ....... H01M 10/0568 429/213
2002/0197468 A1 * 12/2002 Sinko ..................... C09D 5/086 428/458
2004/0157122 A1 * 8/2004 Naoi ..................... H01M 4/602 429/213
2006/0168741 A1 * 8/2006 Laufer .............. C07D 285/125 8/411
2009/0215657 A1 * 8/2009 Ripple ............... C10M 169/048 508/185
2015/0267113 A1 * 9/2015 Ramachandran ....... C23F 11/02 422/16
2018/0316064 A1 * 11/2018 Wei ....................... H01M 10/28
2021/0005937 A1 * 1/2021 Wang .................... H01M 10/36
2021/0226252 A1 * 7/2021 Ha ........................ H01M 4/382
2022/0010453 A1 * 1/2022 Adams .................... H01M 4/38

FOREIGN PATENT DOCUMENTS

CN 108610307 10/2018
CN 109449374 A * 3/2019 .......... H01M 10/058
JP 2004319324 A 11/2004
JP 2012069457 A * 4/2012
WO WO-2018103517 A1 * 6/2018 .......... H01M 50/411
WO WO-2019183224 A1 * 9/2019 ........ H01M 10/0569

OTHER PUBLICATIONS

Yu Ying-Hui, et al., catena-Poly[[tetraaquazinc(II)]-u-1,3,4-thiadiazol-2,5-diyldithiodiacetato-K2O:O], Metal-Organic Compounds, Acta Cryst. Section E Structure Reports Online, Jun. 15, 2008, vol. 64,. No. 6, pp. m794-m794, CrossMark.

Xue, et al., Synthesis, Structures, and Physical Properties of Metal Flexible Dicarboxylate Frameworks with Dipyridyl Coligand, Journal of Molecular Structure, Mar. 21, 2008, vol. 877, No. 1-3, pp. 36-43, Elsevier, Amsterdam, NL.

Wang Xiu-Li, et al., A Series of Flexible bis(imidazole)-based Coordination Polymers Tuned by Central Metal Ions and Dicarboxylates: Diverse Structures and Properties, Inorganica Chimica Acta, Jan. 3, 2014, vol. 412, pp. 104-113, Elsevier BV, NL.

El-Shekeil, Ali G., Poly[di(2,5-dimercapto-1,3,4-thiadiazole)-metal] Complexes of Group IIB: Synthesis, Characterization and DC Electrical Conductivity, May 2008, pp. 121-19, Journal of Macromolecular Science, Part A: Pure and Applied Chemistry, Taylor & Francis Group, LLC.

* cited by examiner

*Primary Examiner* — Imran Akram
(74) *Attorney, Agent, or Firm* — Christopher P. Demas; Michael A. Miller

(57) ABSTRACT

The disclosed technology relates to Zinc salts of 2,5-dimercapto-1,3,4-thiadiazole (“DMTD”), and electrode therewith for use in zinc ion battery systems.

12 Claims, No Drawings

2,5-DIMERCAPTO-1,3,4-THIADIAZOLE (DMTD) ZINC SALT DERIVATIVES

CROSS REFERENCE TO RELATED APPLICATION

This application claims priority from PCT Application Serial No. US21/047272 filed on Aug. 24, 2021, which claims the benefit of U.S. Provisional Application No. 63/070,598 filed on Aug. 26, 2020, the entirety of which is hereby incorporated by reference.

BACKGROUND OF THE INVENTION

The disclosed technology relates to Zinc salts of 2,5-dimercapto-1,3,4-thiadiazole ("DMTD"), and electrodes therewith for use in zinc ion battery systems.

Organic-based electrode materials are relatively new considerations for replacement of inorganic materials as either the positive or negative electrode in a battery. Organic-based materials can be flexible and generally have improved specific capacities and less swelling with cycling than inorganic materials. Organic-based materials are also generally more environmentally friendly than inorganic materials and less expensive.

Some simple alkyl and aryl substituted DMTD derivatives are known, for example, as taught in U.S. Pat. No. 2,736,729, granted Feb. 28, 1956 to Krzikalla et al. and U.S. Pat. No. 3,212,892, granted Oct. 19, 1965, to von Konig et al. Simple acrylic acid alkyl and aryl esters of DMTD are also known, for example, as taught in JP 2013234126, published Nov. 21, 2013 to Oya et al., and U.S. Pat. No. 5,258,395, granted Nov. 2, 1993 to Murase et al.

Examples of organic-based electrode chemistry in the art usually start with some or all of the relatively expensive starting materials and reagents, may need multiple steps to obtain the target final product, generate large quantities of undesirable process wastes, and could also require tedious purification steps. New materials for organic based electrode are desirable.

SUMMARY OF THE INVENTION

The disclosed technology, therefore, solves the problem of difficult to produce and expensive but readily oxidizable organic chemistry by providing new DMTD Zinc salts that can be synthesized in only one or two steps, starting from readily available and inexpensive raw materials, use processing that generates little or no waste, and involve reactions which proceed rapidly and in high product conversions.

In particular, the technology provides a DMTD derivative of formula

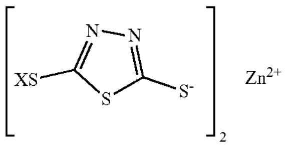

where X is a negative charge or H, or a hydrocarbyl group of 1 to 10 carbon atoms.

The technology also provides an organic-based electrode containing A) at least one polymer binder, B) at least one conductive material, and C) at least one DMTD derivative as discussed herein.

In addition, the technology includes a zinc ion battery system including A) a zinc anode, B) an electrolyte of a solution of a zinc salt, and C) the organic-based electrode disclosed herein.

DETAILED DESCRIPTION OF THE INVENTION

Various preferred features and embodiments will be described below by way of non-limiting illustration.

Provided herein are zinc salt derivatives of 2,5-Dimercapto-1,3,4-thiadiazole ("DMTD"). In general, the DMTD zinc salt derivatives can be represented in the pure form by formula I:

Formula I

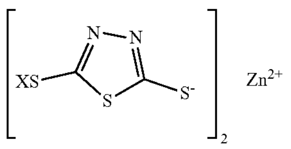

where X is a negative charge or H, or a hydrocarbyl group.

In some instances, X in formula I is a negative charge, in which case, Formula I would be represented by formula I' below:

Formula I'

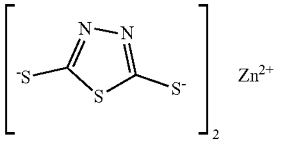

In some instances, X can be H, in which case, Formula I would be represented by formula I" below:

Formula I"

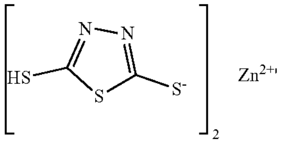

In some embodiments, X in formula I can be a hydrocarbyl group. The hydrocarbyl group can be a hydrocarbyl group of 1 to 10 carbon atoms. X can also be a hydrocarbyl group of 1 to 8 carbon atoms. X can also be a hydrocarbyl group of 1 to 6 carbon atoms.

In some instances, X in formula I can be a hydrocarbyl group in the form of an alkyl group, in which case the alkyl group can have 1 to 10 carbon atoms. Such a compound can be represented by formula I'" below:

Formula I'''

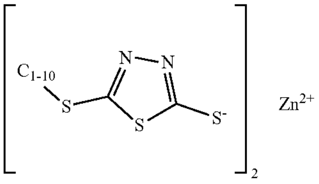

X can also be a hydrocarbyl group in the form of an alkyl group having 1 to 8 carbon atoms. X can also be a hydrocarbyl group in the form of an alkyl group having 1 to 6 carbon atoms.

In some instances, X in formula I can be a hydrocarbyl group in the form of an amide group, in which case the amide group can have 1 to 10 carbon atoms. Such a compound can be represented by formula I'''' below:

Formula I''''

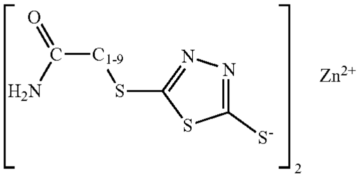

X can also be a hydrocarbyl group in the form of an amide group having 1 to 8 carbon atoms. X can also be a hydrocarbyl group in the form of an amide group having 1 to 6 carbon atoms.

The present technology also includes a zinc electrode containing A) a DMTD derivative as discussed above, B) a polymer binder, and C) a conductive material. As used herein, the term "a," as in "a" DMTD derivative, "a" polymer binder, or "a" conductive material, is not limited to just one of the stated elements, but is used to mean "at least one," which includes one or more of the stated elements, as well as two or more, three or more and so on.

The DMTD derivatives can be present at from about 40 to 80 wt. % of the electrode composition. The DMTD derivatives can be present at from about 45 to 75 wt. % of the electrode composition. The DMTD derivatives can be present at from about 50 to 70 wt. % of the electrode composition. The DMTD derivatives can be present at from about 55 to 65 wt. % of the electrode composition.

The polymer binders useful in the electrode are well known and not particularly limited in the instant zinc electrode composition. The binder is preferably made of a material conventionally known as a binder contained in a positive electrode mixture and is, for example, preferably PVDF (polyvinylidene difluoride). Other examples of polymeric binders used in electrodes include, for example, polyamide-imides, polytetrafluoroethylenes ("PTFE"), and polyamides. Other example binders include carboxymethyl cellulose ("CMC") and styrene-butadiene rubbers ("SBR").

The polymer binder may be present at from about 1 to 20 wt. % of the electrode composition. The polymer binder may be present at from about 2.5 to 15 wt. % of the electrode composition. The polymer binder may be present at from about 5 to 10 wt. % of the electrode composition.

As with the polymer binder, the conductive materials are well known and not particularly limited in the instant zinc electrode composition. The conductive material is preferably made of a material conventionally known as a conductive material contained in a positive electrode mixture and is, for example, preferably a carbon material, such as carbon black or its subtypes, including acetylene black, channel black, furnace black, lamp black, thermal black and mixtures thereof. Other examples of conductive material include vapor-grown carbon fibers (VGCF), graphite, and highly ordered mesoporous carbons (OMC). Such a conductive materials can be employed alone, or two or more types of conductive materials can be combined.

The conductive material may be present at from about 10 to 40 wt. % of the electrode composition. The conductive material may be present at from about 15 to 35 wt. % of the electrode composition. The conductive material may be present at from about 20 to 30 wt. % of the electrode composition.

The zinc electrodes may be formed by standard methods known in the art. For example, the ingredients may be formed into a paste, for example, in a mortar and pestle or by other mechanical means, and then applied to the desired region of a zinc battery and allowed to dry. Alternatively, wet granulated particles containing the zinc electrode ingredients may be pressure-bonded to the desired region in the battery and allowed to dry.

The present technology also includes a zinc ion battery system. The zinc ion battery system includes A) the zinc electrode discussed above, B) a zinc anode, and C) an electrolyte containing a solution of a zinc salt.

The zinc anode is simply a bar of zinc used as a sacrificial anode. Such zinc anodes are commercially available.

The electrolyte contains a solution of a zinc salt. The solution of the zinc salt may be a solution in a polar solvent. The polar solvent can be any solvent in which the zinc salt is soluble. The polar solvent should also remain inert within the working conditions of the zinc batter. It is expected that those of ordinary skill can readily determine the solubility and inertness of, and therefore choose, the appropriate solvent. The simplest solvent for the present technology would be water and in an embodiment, the technology indeed provides an aqueous zinc ion battery system including A) the zinc electrode discussed above, B) a zinc anode, and C) an electrolyte containing an aqueous solution of a zinc salt.

In some embodiments, the polar solvent can also be, for example, an alcohol, such as $C_1$ to $C_{10}$ alcohol or glycol, including, for example, methanol, ethanol, 1-propanol, 2-propanol, ethylene glycol, propylene glycol. Ethers may also be employed as the solvent, including, for example, dimethoxymethane, methoxybenzene (anisole), tetrahydrofuran (THF), 2-methyltetrahydrofuran, 1,4-dioxane, 1,3-dioxolane (DOL), 4-methyl-1,3-dioxolane, 1,2-dimethoxyethane (DME), and bis(2-methoxyethyl) ether (diglyme). The polar solvent can also be a ketone, such as acetone or acetylacetone. Nitriles, such as, for example, acetonitrile (ACN), methoxyacetonitrile, propionitrile, butyronitrile, isobutyronitril, benzonitrile, and 3-methoxypropionitrile can be employed as the solvent, as can amines, such as ethylenediamine and pyridines, or amides such as formamide, n-methylacetamide, N,N-dimethylformamide (DMF), N,N-dimethylacetamide (DMA), and N-methyl-2-pyrrolidinone (NMP). The solvent can also be a carbonate. Non-limiting examples of carbonates include propylene carbonate (PC), ethylene carbonate (EC), dimethyl carbonate (DMC), diethyl carbonate (DEC), ethyl methyl carbonate (EMC), and 1,2-butylene carbonate. The solvent can also be a cyclic ester such as γ-butyrolactone (γ-BL) or γ-valerolactone (γ-VL). Other organic based solvents are also contemplated, such as, for example, hexane, benzene, toluene, nitromethane, nitrobenzene, 1,2-dichloroethane, dimethyl sulfoxide (DMSO), ethyl acetate, and nitroethane to name a few. The solvent may also employ a combination of any of the foregoing solvents.

Zinc salts are well known, commercially available and not particularly limited in the instant technology. The zinc salt of the electrolyte can be for example, zinc sulfate ($ZnSO_4$), zinc trifluoromethanesulfonate (Zn(OTf)) and combinations thereof. Other examples of zinc salts include, zinc halogens, such as zinc bromide, zinc iodide, zinc fluoride, and zinc chloride, zinc carboxylates, such as zinc acetate, zinc citrate, zinc ricinoleate, zinc methacrylate, zinc oxalate and the like, zinc nitrates, zinc cyanide, zinc phosphates, zinc molybdates, zinc chromates, zinc silicates, such as zinc hexafluorosilicate and many others.

The zinc salt may be present in the electrolyte solution at from about a 0.05 M to 5 M concentration. The zinc salt may be present in the electrolyte solution at from about a 0.25 M to 4 M concentration. The zinc salt may be present in the electrolyte solution at from about a 0.5 M to 3 M concentration. The zinc salt may be present in the electrolyte solution at from about a 0.75 M to 3 M concentration.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

EXAMPLES

Example 1. Synthesis of Poly-[Zinc-1,3,4-Thiadiazole-2,5-dithiolate]—42.86 g of dipotassium-1,3,4-Thiadiazole-2,5-dithiolate from Sigma Aldrich was dissolved in 300 g of deionized water and 25.8 g of zinc chloride added. The reaction was stirred at 75° C. for four hours under a nitrogen atmosphere after which time a white solid precipitated from solution. The solid was filtered and washed to remove potassium chloride by-product and dried in a vacuum oven. The product yield was 37.2 g.

Example 2. Synthesis of 5-(methylthio)-1,3,4-thiadiazole-2(3H)-thione—The procedure of Van de Mark[1] was used with minor modifications. 56.1 g of KOH and 900 g of ethanol were added to a 3-L flask and the mixture heated at 50 deg C. for 2 hrs. The reaction was cooled to 10° C. in an ice-water bath and 150.2 g of 2,5-dimercapto-1,3,4-thiadiazole (DMTD) was added in portions over 20 minutes. The reaction mixture was heated at 60° C. for 3 hours and then cooled to room temperature. 142 g of methyl iodide was added at 15° C. over 20 minutes and the mixture was heated at reflux (78° C.) for 6 hours. Around one half of the reaction mixture was distilled to remove solvent and the remaining solution cooled, and then partitioned between water and toluene in a separatory funnel. The toluene phase was collected, dried over anhydrous magnesium sulfate, and concentrated on a rotary evaporator to obtain the crude product. $^{13}C$ NMR showed a mixture of mono- and dimethylated product was obtained. Recrystallization from reagent grade toluene afforded 64 g of the final product as a 13:87 mole mixture of dimethylated and the desired monomethylated DMTD. (1.) Van de Mark, M. et. al.: 5-Mercapto-1,3,4-Thiadiazole-2(3H)-thione: Synthesis and Structure of Alkylated Derivatives. *J. Heterocyclic Chem.*, 2014, 51, p747.

Example 3. Synthesis of Zinc-bis-(2-Methylthio)-1,3,4-thiadiazole-5-thiolate-22.8 g of the crude 5-(methylthio)-1,3,4-thiadiazole-2(3H)-thione prepared in Example 2 was dissolved in 250 g of deionized water and 7.8 g of potassium hydroxide added. The reaction was heated under a nitrogen atmosphere at 80° C. for four hours and cooled. In a separatory funnel, the aqueous solution was washed with two 75 mL portions of reagent grade toluene to remove the dialkylated DMTD contaminant, collected, and transferred to a 500 mL round bottom flask. 9.1 g of zinc chloride was added and the mixture heated at 75° C. under nitrogen for four hours. After cooling, the white precipitate was filtered, washed with DI water, and dried in a vacuum oven to yield 25.7 g.

Example 4. Synthesis of 2-Isoamylthio-5-thiol-1,3,4-thiadiazole-150.2 g of 2,5-dimercapto-1,3,4-thiadiazole and 500 mL of ethanol were added to a 2-L flask and 56.1 g of potassium hydroxide was added. The reaction was heated at 77° C. for three hours under nitrogen and cooled to room temperature. 151.05 g of isoamyl bromide was added and the mixture heated at 77° C. for six hours. Around 80% of the ethanol was distilled. The reaction mixture was cooled and transferred to a 2-L separatory funnel containing 400 g of water and 600 mL of reagent grade toluene. After washing thoroughly with more water, the organic top phase was collected, dried over anhydrous sodium sulfate, filtered, and vacuum stripped on a rotary evaporator to obtain 218 g of a low-melting solid. $^{13}C$ NMR showed mostly mono-alkylate was present with some di-alkylate. The solid was recrystallized from reagent grade toluene:methanol (80:20) wt. and dried in a vacuum oven. The final product yield was 135 g.

Example 5. Synthesis of 2-(2-Amidoethylthio)-5-thiol-1,3,4-thiadiazole-180.3 g of 2,5-dimercapto-1,3,4-thiadiazole and 0.4 g of sodium hydroxide were added to 900 g of deionized water in a 2-L flask. 85.3 g of acrylamide was added and the mixture heated at 90° C. for 12 hours. The insoluble product was collected by filtration with a sintered glass funnel and washed with 0.5 L of fresh deionized water followed by drying in a vacuum oven. The yield of final product was 259 g.

Using a procedure similar to Example 3, the corresponding zinc salts were prepared from Examples 4 and 5:

Example 6. Zinc-bis-(2-Isoamythio)-1,3,4-thiadiazole-5-thiolate

Example 7. Zinc-bis-(2-(2-Amidoethylthio)-1,3,4-thiadiazole-5-thiolate

The table below provides the galvanostatic cycling experiments of coin cells of several of the example zinc DMTD samples using 1M $ZnSO_4$ aqueous electrolyte solution and Zn foil as anode.

Coin cell preparation: Electrode dry mixtures were prepared by mixing powders of the example zinc DMTD noted in the table below with conductive carbon black (SuperP™, available from Imerys) and polyvinylidene fluoride (PVDF) binder in a 70:20:10 weight ratio using a mortar and pestle. The dry electrode powder (ca. 8-12 mg) was directly cast in the coin cell casing. Coin-type cells were assembled in air with cathode powder, 1 M aqueous solution of $ZnSO_4$ as the electrolyte, Nafion™ and/or GFA as the separator, and Zn foil as the anode. Coin cells were assembled bottom to top using materials purchased from Gelon: coin cell bottom, cathode powder, 50 μL electrolyte, Nafion™ and/or GFA separator, 50 μL electrolyte, Zn anode, stainless steel current collector, wave/conical washer, coin cell top with gasket. Coin cells were crimped in a Gelon GN-CCM20 coin cell crimper at 900 psi and used for battery testing after a rest period of 2 hours.

The assembled Coin-type cells were subjected to galvanostatic cycling using an automated testing system with lower voltage limits of 0.7 V (vs. Zn) and upper voltage limits of 1.8V (vs. Zn). The currents for galvanostatic measurements were calculated based on the theoretical specific capacity of each compound.

Theoretical capacity=F/(3600*MW); F is Faraday constant, MW is molecular weight C rate: refers to the current used for galvanostatic cycling.

Max capacity is the max capacity achieved/theoretical capacity. [Max capacity achieved] is the capacity achieved when the discharge hits lower voltage cut-off.

Decay/cycle is estimated based *on* capacity fading(in *mAh/g*)/cycle=(capacity of the first cycle−capacity of the last cycle)/(cycle number*capacity of the first cycle)

Voltage gap is the voltage difference between the charging plateau and discharge plateau When the battery is charged or discharged at a steady voltage it is referred to, respectively, as charging plateau and discharge plateau.

| Identity | Theoretical Capacity | Membrane | Cycling C Rate | Maximum Capacity | Decay/ Cycle | Current | Voltage Gap |
|---|---|---|---|---|---|---|---|
| Example 1 | 250.1 mAh/g | 2x GFA | 0.29 C | 60% | 26% | 1 mA | 0.8 V |
| Example 3 | 136.8 mAh/g | Nafion + GFA | 0.5 C | 87% | <1% | 0.632 mA | 0.20 V |
| | | GFA | 0.5 C | 84% | 1% | 0.551 mA | 0.25 V |
| | | Nafion + GFA | 1 C | 73% | <1% | 0.996 mA | 0.30 V |
| | | Nafion + GFA | 0.2 C | 93% | >1% | 0.218 mA | 0.15 V |

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

A DMTD Derivative of Formula

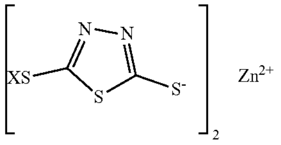

where X is a negative charge or H, or a hydrocarbyl group of 1 to 10 carbon atom. The DMTD derivative of the previous sentence where X is a hydrocarbyl group of 1 to 8 carbon atoms. The DMTD derivative of the previous sentence where X is a hydrocarbyl group of 1 to 6 carbon atoms.

The DMTD derivative of the previous paragraph, wherein the hydrocarbyl group comprises an alkyl group or an amide group.

The DMTD derivative of any sentence of any previous paragraph, wherein the derivative is of formula:

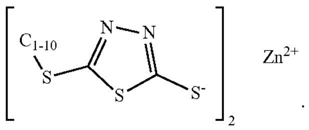

The DMTD derivative of any sentence of any previous paragraph, wherein the derivative is of formula:

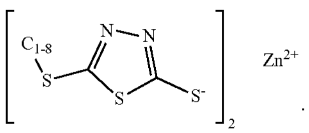

The DMTD derivative of any sentence of any previous paragraph, wherein the derivative is of formula:

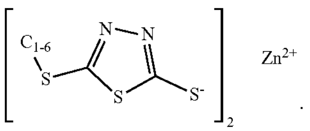

The DMTD derivative of any sentence of any previous paragraph, wherein the derivative is of formula:

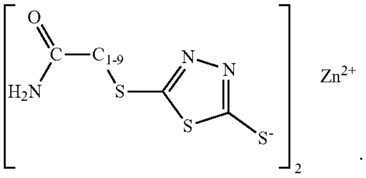

The DMTD derivative of any sentence of any previous paragraph, wherein the derivative is of formula:

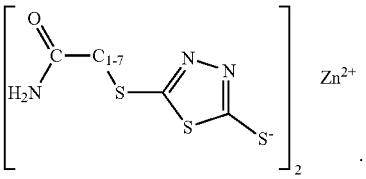

The DMTD derivative of any sentence of any previous paragraph, wherein the derivative is of formula:

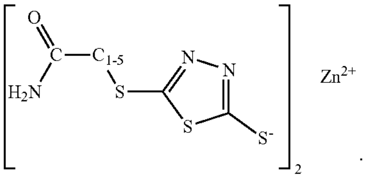

A zinc electrode comprising A) a DMTD derivative of any sentence of any previous paragraph, B) a polymer binder, and C) at least one conductive material.

The zinc electrode of sentence of any previous paragraph, wherein the DMTD or derivative thereof is present at from about 40 to 80 wt. % of the electrode composition.

The zinc electrode of sentence of any previous paragraph, wherein the DMTD or derivative thereof is present at from about 45 to 75 wt. % of the electrode composition.

The zinc electrode of sentence of any previous paragraph, wherein the DMTD or derivative thereof is present at from about 50 to 70 wt. % of the electrode composition.

The zinc electrode of sentence of any previous paragraph, wherein the DMTD or derivative thereof is present at from about 55 to 65 wt. % of the electrode composition.

The zinc electrode of any sentence of any previous paragraph, wherein the polymer binder is present at from about 1 to 20 wt. % of the electrode composition.

The zinc electrode of any sentence of any previous paragraph, wherein the polymer binder is present at from about 2.5 to 15 wt. % of the electrode composition.

The zinc electrode of any sentence of any previous paragraph, wherein the polymer binder is present at from about 5 to 10 wt. % of the electrode composition.

The zinc electrode of any sentence of any previous paragraph, wherein the polymer binder is PVDF, styrene-butadiene rubber.

The zinc electrode of any sentence of any previous paragraph, wherein the conductive material is present at from about 10 to 40 wt. % of the electrode composition.

The zinc electrode of any sentence of any previous paragraph, wherein the conductive material is present at from about 15 to 35 wt. % of the electrode composition.

The zinc electrode of any sentence of any previous paragraph, wherein the conductive material is present at from about 20 to 30 wt. % of the electrode composition.

The zinc electrode of any sentence of any previous paragraph, wherein the conductive material is conductive carbon black.

A zinc ion battery system comprising A) a zinc anode, B) an electrolyte comprising a solution of a Zinc salt, and C) the zinc electrode of any sentence of any previous paragraph.

The zinc ion battery of any sentence of any previous paragraph, wherein the zinc salt of the electrolyte comprises at least one of zinc sulfate ($ZnSO_4$), Zinc trifluoromethanesulfonate (Zn(OTf)) and combinations thereof.

The zinc ion battery of any sentence of any previous paragraph, wherein the concentration of the zinc salt in the electrolyte is 0.05 M to 5 M.

The zinc ion battery of any sentence of any previous paragraph, wherein the concentration of the zinc salt in the electrolyte is 0.25 M to 4 M.

The zinc ion battery of any sentence of any previous paragraph, wherein the concentration of the zinc salt in the electrolyte is 0.5 M to 3.5 M.

The zinc ion battery of any sentence of any previous paragraph, wherein the concentration of the zinc salt in the electrolyte is 0.75 M to 3 M.

What is claimed is:

1. A zinc ion battery system comprising A) a zinc anode, B) an electrolyte comprising a solution of a Zinc salt, and C) a zinc electrode comprising I) a DMTD derivative of formula

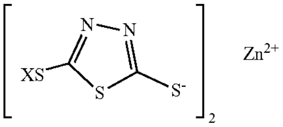

where X is a negative charge or H, or a hydrocarbyl group of 1 to 10 carbon atoms II) a polymer binder, and III) at least one conductive material.

2. The zinc ion battery system of claim 1, wherein the hydrocarbyl group comprises an alkyl group or an amide group.

3. The zinc ion battery system of claim 1, wherein the derivative is of formula:

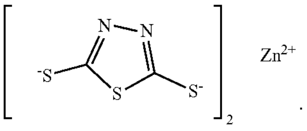

4. The zinc ion battery system of claim 1, wherein the derivative is of formula:

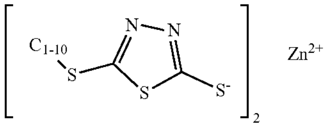

5. The zinc ion battery system of claim 1, wherein the derivative is of formula:

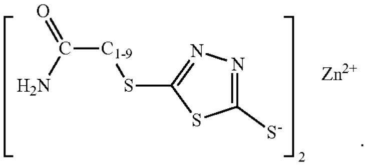

.

6. The zinc ion battery system of claim 1, wherein the DMTD or derivative thereof is present at from about 40 to 80 wt. % of the electrode composition.

7. The zinc ion battery system of claim 1, wherein the polymer binder is present at from about 1 to 20 wt. % of the electrode composition.

8. The zinc ion battery system claim 1, wherein the polymer binder is PVDF, styrene-butadiene rubber.

9. The zinc ion battery system of claim 1, wherein the conductive material is present at from about 10 to 40 wt. % of the electrode composition.

10. The zinc ion battery system of claim 1, wherein the conductive material is carbon black.

11. The zinc ion battery of claim 1, wherein the zinc salt of the electrolyte comprises at least one of zinc sulfate ($ZnSO_4$), Zinc trifluoromethanesulfonate (Zn(OTf)) and combinations thereof.

12. The zinc ion battery of claim 1, wherein the concentration of the zinc salt in the electrolyte is 0.05 M to 5 M.

* * * * *